United States Patent [19]

Komatsu et al.

[11] Patent Number: 4,632,782
[45] Date of Patent: Dec. 30, 1986

[54] OXIDIZING AN ORGANIC COMPOUND

[75] Inventors: Tatsuyoshi Komatsu, Kamakura; Shigeaki Numata; Katsuhiko Hioki, both of Yokohama; Toshihiko Sumino, Kawasaki, all of Japan

[73] Assignee: Kawasaki Kasei Chemicals Limited, Tokyo, Japan

[21] Appl. No.: 603,790

[22] Filed: Apr. 25, 1984

[30] Foreign Application Priority Data

May 26, 1983 [JP] Japan ................................. 58-91452

[51] Int. Cl.$^4$ ..................... C07C 50/08; C07C 50/12
[52] U.S. Cl. ................................ 260/396 R; 260/365; 260/369; 260/385; 260/687 H
[58] Field of Search .................. 260/396 R, 365, 369, 260/385, 687

[56] References Cited

U.S. PATENT DOCUMENTS 3,873,580  3/1975  Rennie III ...................... 260/396 R

FOREIGN PATENT DOCUMENTS

| 1132996 | 10/1982 | Canada ............................... 260/396 |
| 27400 | 4/1981 | European Pat. Off. ......... 260/396 R |
| 75828 | 4/1983 | European Pat. Off. ............. 260/396 |
| 49-34978 | 9/1974 | Japan .............................. 260/396 R |
| 56-61321 | 5/1981 | Japan .............................. 260/396 R |
| 19178 | of 1903 | United Kingdom ................. 260/385 |
| 1192037 | 5/1970 | United Kingdom ............ 260/396 R |
| 1203434 | 8/1970 | United Kingdom ............ 260/396 R |
| 1360904 | 7/1974 | United Kingdom ................ 260/385 |

OTHER PUBLICATIONS

Trahanovsky et al., J. Chem. Soc., 1966, pp. 5777-5778, "Controlled Oxidations of Organic Compounds with Cerium (IV)".
Periasamy & Bhatt, Tetrahedron Letter, No. 27, pp. 2357-2360, 1977.
M. Periasamy et al., Chemical Abstracts, vol. 88, No. 3, 1/16/78, 22436r, p. 593, "A New 1,2-Shift in the Oxidation of Aromatic Rings".

Primary Examiner—Glennon H. Hollrah
Assistant Examiner—Raymond Covington
Attorney, Agent, or Firm—Oblon, Fisher, Spivak, McClelland & Maier

[57] ABSTRACT

A process for oxidizing an organic compound by ceric sulfate dissolved in an aqueous sulfuric acid solution, wherein the organic compound is oxidized (1) by means of a ceric sulfate-aqueous sulfuric acid solution or a cerous sulfate-containing ceric sulfate-aqueous sulfuric acid solution in which the molar concentration (mol/-liter) of ceric sulfate is at least the molar concentration of cerium (ions) contained in the molecules of cerous sulfate at the maximum solubility of cerous sulfate in an aqueous sulfuric acid solution at the final sulfuric acid concentration (exclusive of ceric sulfate and cerous sulfate) and at the temperature under the oxidation reaction conditions and at most the saturated molar concentration of ceric sulfate in said aqueous sulfuric acid solution, (2) under a condition such that at the end of the oxidation reaction, the concentration of ceric sulfate is maintained at a level capable of dissolving cerous sulfate which is present at a concentration of at least the maximum solubility of cerous sulfate in said aqueous sulfuric acid solution.

7 Claims, 4 Drawing Figures

4,632,782

OXIDIZING AN ORGANIC COMPOUND

BACKGROUND OF THE INVENTION

1. Field of the Invention

The present invention relates to a process for oxidizing an organic compound such as naphthalene by means of a ceric sulfate-aqueous sulfuric acid solution, to obtain an oxidation product of the organic compound such as 1,4-naphthoquinone industrially advantageously.

2. Discussion of the Background

It is well known to oxidize an organic compound such as naphthalene by means of an aqueous acid solution of a ceric compound. For instance, as industrial processes, there may be mentioned (1) a process wherein a polynuclear aromatic hydrocarbon dissolved in a water-immiscible organic solvent, is oxidized by means of a ceric salt-aqueous acid solution such as a ceric sulfate-aqueous sulfuric acid solution to obtain a quinone corresponding to the polynuclear aromatic hydrocarbon (Japanese Examined Patent Publication No. 34978/1974), (2) a process wherein powdery naphthalene is reacted while it is suspended in an aqueous solution of a ceric salt by means of a dispersing agent (Japanese Unexamined Patent Publication No. 61321/1981), and (3) other processes such as a process for producing from toluene or its substituted derivative a corresponding benzaldehyde, and a process for producing from a secondary alcohol a corresponding ketone [Walters Trahanovsky et al., J. Chem. Soc., 1966, pages 5777–5778; Koichiro Ohshima, Journal of Organic Synthetic Chemistry Association, 40(12), pages 1171–1179 (1982)]. As the ceric compound-aqueous acid solution to be used for the oxidation reaction in these processes, it is particularly advantageous from the industrial point of view to employ a ceric sulfate-aqueous sulfuric acid solution which has relatively low corrosiveness, contains little by-products, and is industrially readily available at low cost, taking into consideration a step of electrochemical regeneration which is commonly employed as a method for regenerating the resulting cerous salt into the ceric salt, after the oxidation reaction.

However, the conventional oxidation reaction with use of a ceric compound is usually conducted at a concentration lower than the maximum solubility of the cerium compound. For instance, the ceric sulfate concentration in a ceric sulfate-aqueous sulfuric acid solution used to be limited to a low level of from 0.25 to 0.278 mol/liter, since the solubility of cerous sulfate resulting from the oxidation reaction with the ceric sulfate is relatively small. In addition, when the cerous sulfate resulting from the oxidation reaction is to be regenerated as ceric sulfate by electrochemical oxidation, the current efficiency is largely dependent on the concentration of cerous sulfate as shown in FIG. 4, according to the experimental results by the present inventors. Therefore, when electrolysis cost constitute a substantial portion of the price of the product, a predetermined amount of cerous sulfate will remain in the regenerated ceric sulfate solution in order to increase the current efficiency. When cerous sulfate remains, the effective amount per unit volume of ceric sulfate used in the respective reactions in the conventional processes, will decrease, and it will be necessary to enlarge the reactor and the accompanying installations, thus leading to industrial difficulties. The industrial application of the method for the oxidation of an organic compound by means of a ceric sulfate-aqueous sulfuric acid solution has been prevented by such industrial difficulties inherent to the conventional processes.

SUMMARY OF THE INVENTION

The present inventors have conducted extensive research to solve such industrial difficulties inherent to the conventional processes. As a result, it has been found that while the solubility of ceric sulfate is not substantially affected by the concentration of cerous sulfate, the solubility of cerous sulfate increases as the concentration of ceric sulfate increases. Accordingly, it is possible to substantially increase over the conventional processes the ceric sulfate concentration effective for the reaction per unit volume if the organic compound is oxidized by means of a ceric sulfate-aqueous sulfuric acid solution having a ceric sulfate concentration of at least the concentration used to be employed by the conventional processes, particularly at least the saturated concentration, and at the end of the reaction, ceric sulfate is maintained at a concentration sufficient to prevent the precipitation of cerous sulfate, whereby it is possible to readily resolve the above-mentioned industrial difficulties inherent to the conventional processes. The present invention has been accomplished based on these discoveries.

Namely, the present invention provides a process for oxidizing an organic compound by ceric sulfate dissolved in an aqueous sulfuric acid solution, wherein the organic compound is oxidized (1) by means of a ceric sulfate-aqueous sulfuric acid solution or a cerous sulfate-containing ceric sulfate-aqueous sulfuric acid solution in which the molar concentration (mol/liter) of ceric sulfate is at least the molar concentration of cerium (ions) contained in the molecules of cerous sulfate at the maximum solubility of cerous sulfate in an aqueous sulfuric acid solution at the final sulfuric acid concentration (exclusive of ceric sulfate and cerous sulfate) and at the temperature under the oxidation reaction conditions and at most the saturated molar concentration of ceric sulfate in said aqueous sulfuric acid solution, (2) under a condition such that at the end of the oxidation reaction, the concentration of ceric sulfate is maintained at a level capable of dissolving cerous sulfate which is present at a concentration of at least the maximum solubility of cerous sulfate in said aqueous sulfuric acid solution.

Now, the present invention will be described in detail with reference to the preferred embodiments.

BRIEF DESCRIPTION OF THE FIGURES

In the accompanying drawings.

FIG. 1 illustrates the solubility at 50° C. in a 6% sulfuric acid aqueous solution.

FIG. 2 illustrates the solubility at 50° and 80° C. in a 10% sulfuric acid aqueous solution.

FIG. 3 illustrates the solubility at 50° and 80° C. in a 14% sulfuric acid aqueous solution.

DETAILED DESCRIPTION OF THE PREFERRED EMBODIMENTS

In the present invention, the organic compound used as a starting material to be oxidized, may be any organic compound which can be oxidized by means of a ceric sulfate-aqueous sulfuric acid solution. Specifically, there may be mentioned unsubstituted or substituted compounds of polynuclear aromatic hydrocarbons such as naphthalene, anthracene, diphenyl, pyrene, phenanthrene, α-nitronaphthalene and 2-ethylanthracene; toluene and its derivatives such as toluene, xylene, p-nitrotoluene and p-methoxytoluene; and a secondary alcohol such as 4-dodecanol. When these organic compounds are oxidized by the process of the present invention, there may be obtained, for instance, in the case of the unsubstituted or substituted compounds of polynuclear aromatic hydrocarbons, 1,4-naphthoquinone from naphthalene, anthraquinone from anthracene, 2-phenylbenzoquinone from diphenyl, pyrenequinone from pyrene, 9,10-phenanthraquinone from phenanthrene, 5-nitro-1,4-naphthoquinone from α-nitronaphthalene, and 2-ethylanthraquinone from 2-ethylanthracene; benzaldehyde and its derivatives from toluene and its derivatives; and a ketone such as 4-dodecanone from the secondary alcohol such as 4-decanol.

The ceric sulfate to be used in the present invention may be the one obtained by a process of dissolving a ceric compound such as ceric oxide in sulfuric acid. Industrially, however, there may be used an aqueous sulfuric acid solution of ceric sulfate obtained by regenerating cerous sulfate formed by the oxidation reaction of the above-mentioned unsubstituted or substituted hydrocarbon compound or its derivative with ceric sulfate, for instance, by electrolytic oxidation.

Now, the oxidation reaction of naphthalene with ceric sulfate and the regeneration reaction of the resulting cerous sulfate to ceric sulfate by electrolytic oxidation, are shown by the following formulas. By the reaction (a), 1 mole of cerous sulfate and 1 mole of sulfuric acid will be formed from 2 moles of ceric sulfate.

Reaction (a):

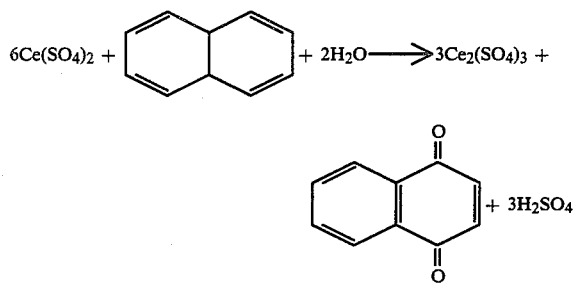

Regeneration (b):

$3Ce_2(SO_4)_3 + 3H_2SO_4 \rightarrow 6Ce(SO_4)_2 + 3H_2$

Figure 1:
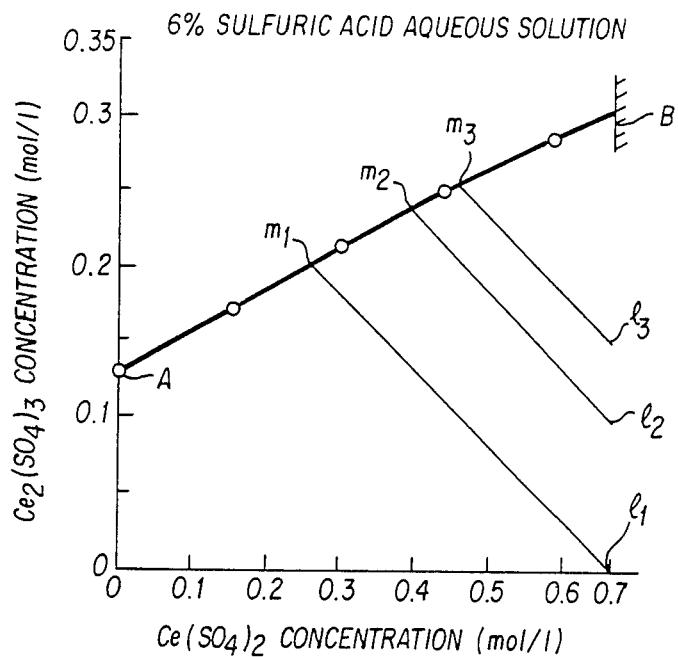
FIGS. 1 to 3 are graphs illustrating the solubility of cerous sulfate relative to the concentration of ceric sulfate in an aqueous sulfuric acid solution.
Figure 2:
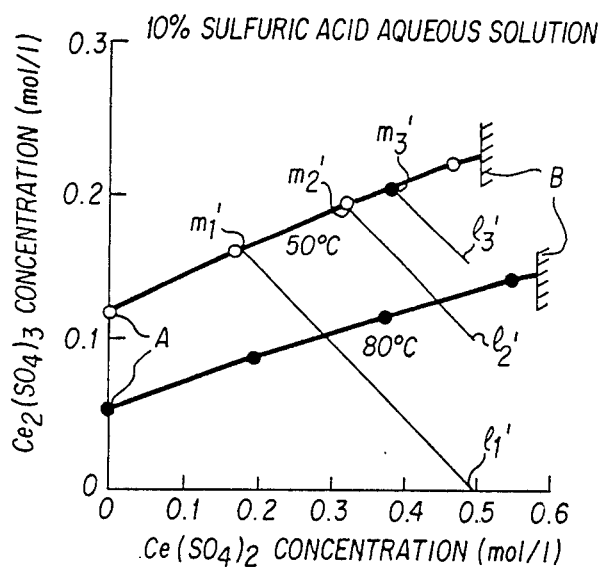
Figure 3:
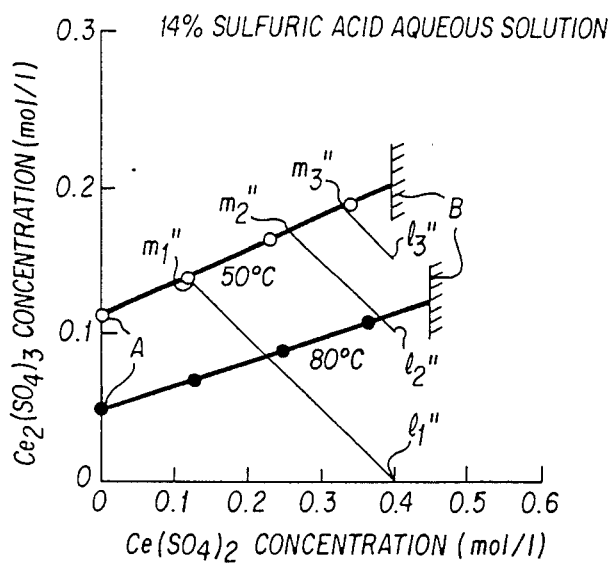

In the present invention, the sulfuric acid concentration in the aqueous sulfuric acid solution gives an influence over the solubility of cerous sulfate and ceric sulfate, as is evident from FIGS. 1 to 3. As shown by the above reaction formula, the concentration of sulfuric acid increases by about 1.5% from the concentration prior to the reaction to the concentration after the reaction. In general, the concentration of sulfuric acid at the final stage of the reaction (hereinafter referred to simply as a "final concentration") is preferably from about 5 to about 15% by weight, more preferably from about 6 to about 12% by weight, especially from about 6 to about 10% by weight. If the final concentration of sulfuric acid is lower than about 5%, ceric sulfate tends to undergo hydrolysis and becomes unstable. On the other hand, if the final concentration exceeds about 15%, the solubility of ceric sulfate tends to decrease, such being undesirable.

The reaction temperature is usually from 40° to 80° C., preferably from 40° to 60° C. If the reaction temperature is lower than 40° C., the solubility of ceric sulfate tends to decrease and the reaction velocity likewise tends to decrease. If the temperature exceeds 80° C., the solubility of cerous sulfate tends to decrease, and ceric sulfate tends to undergo hydrolysis and becomes to be unstable, and the loss of heat energy increases.

In the present invention, the molar concentration (mol/liter) of ceric sulfate in the ceric sulfate-aqueous sulfuric acid solution to be supplied for the oxidation reaction, i.e. prior to the oxidation reaction, should preferably be as high as possible so that the total amount of liquid can be minimized. In order to set the molar concentration of the ceric sulfate at a level of at least the concentration disclosed by the conventional processes and as high as possible, it is selected within a range of at most the saturated molar concentration of ceric sulfate and at least the molar concentration of cerium (ions) contained in the molecules of cerous sulfate at the maximum solubility of cerous sulfate in the aqueous sulfuric acid solution at the final concentration and at the temperature under the above oxidation reaction conditions. The lower limit of the molar concentration of ceric sulfate, i.e. the molar concentration of cerium (ions) contained in the molecules of cerous sulfate at the maximum solubility of cerous sulfate in the aqueous sulfuric acid solution, corresponds to twice the saturated molar concentration (i.e. the solubility) of cerous sulfate ($Ce_2(SO_4)_3$) as indicated at point A in each of FIGS. 1 to 3 [showing the relationship between the molar concentration of ceric sulfate and the solubility (i.e. the saturated molar concentration) of cerous sulfate in an aqueous sulfuric acid solution at the predetermined temperature and concentration] where the molar concentration of ceric sulfate ($Ce(SO_4)_2$) is zero. This means that since one molecule of cerous sulfate ($Ce_2(SO_4)_3$) contains two cerium atoms, the molar concentration of cerium (ions) of cerous sulfate corresponds to twice the molar concentration of ceric sulfate ($Ce(SO_4)_2$) which contains one cerium atom in one molecule. Specifically, the lower limit of the molar concentration of ceric sulfate is (a) 0.125×2=0.25 mol/liter in the case of a 6% sulfuric acid aqueous solution at 50° C. as shown at point A in FIG. 1 where the saturated molar concentration of cerous sulfate ($Ce_2(SO_4)_3$) is 0.125 mol/liter, (b) 0.115×2=0.23 mol/liter in the case of a 10% sulfuric acid aqueous solution at 50° C. as shown at point A in FIG. 2, or (c) 0.11×2=0.22 mol/liter in the case of a 14% sulfuric acid aqueous solution at 50° C. as shown at point A in FIG. 3. Thus, for the industrial operation, when the concentration of the aqueous sulfuric acid solution is from about 6 to about 10% by weight and the reaction temperature is from 40° to 60° C., the concentration of ceric sulfate prior to the oxidation reaction, is preferably selected within a range of at least 0.28 mol/liter, more preferably at least 0.3 mol/liter, still more preferably at least 0.35 mol/liter and at most the saturation concentration.

In the present invention, it is more advantageous for the purpose of accomplishing the object of the present invention that the ceric sulfate-aqueous sulfuric acid solution contains no cerous sulfate prior to the oxidation reaction with ceric sulfate. However, as mentioned above, when the cerous sulfate resulting from the oxidation reaction, is to be regenerated as ceric sulfate by electrolytic oxidation, it is not desirable that the cerous sulfate content is too low since the current efficiency will be poor. For instance, even when the electrolysis is conducted at a high linear velocity of the flow of the electrolyte of about 0.4 m/sec, the current efficiency will be remarkably poor if the concentration of cerous sulfate is lower than 0.006-0.1 mol/liter. Accordingly, the concentration of cerous sulfate prior to the oxidation reaction with ceric sulfate is preferably at least 0.06 mol/liter, more preferably at least 0.08 mol/liter, still more preferably at least 0.1 mol/liter and preferably at most 0.18 mol/liter, more preferably at most 0.15 mol/liter. If the cerous sulfate concentration exceeds 0.18 mol/liter, the effective amount of ceric sulfate to be used for the oxidation reaction, decreases, such being undesirable.

In the present invention, it is necessary to conduct the reaction so that at the end of the oxidation reaction with ceric sulfate, the molar concentration of cerous sulfate in the aqueous sulfuric acid solution is at least the molar concentration corresponding to the maximum solubility in the aqueous sulfuric acid solution at the final concentration and at the temperature under the oxidation reaction conditions (e.g. corresponding to the solubility of $Ce_2(SO_4)_3$ shown at point A in each of FIGS. 1 to 3 as mentioned above), and yet it is necessary to maintain the concentration of ceric sulfate at a level capable of dissolving cerous sulfate at such a molar concentration. However, from the industrial point of view, the molar concentration of cerous sulfate is desired to be small in order to maximize the effective amount of ceric sulfate and to minimize the total amount of liquid for the oxidation reaction according to the process of the present invention, while the molar concentration of cerous sulfate is required to be increased to improve the current efficiency of the electrolytic oxidation for regeneration. The molar concentration of cerous sulfate at the end of the oxidation reaction according to the process of the present invention, which may be employed for an industrial operation as satisfying the above conditions, may be selected usually within a range of from 0.13 to 0.30 mol/liter, preferably from 0.15 to 0.25 mol/liter, although it depends on the reaction temperature and the sulfuric acid concentration.

According to the process of the present invention, no cerium salt is precipitated by the oxidation reaction, and accordingly the process can be applied to the method wherein the oxidation is conducted by dissolving the starting material with use of an organic solvent immiscible with water (Japanese Examined Patent Publication No. 34978/1974) or to the method wherein the oxidation is conducted by dispersing powdery naphthalene (Japanese Unexamined Patent Publication No. 61321/1981). Further, the process of the present invention is particularly outstanding in that as shown in Table 1 given hereinafter, the maximum effective amount of ceric sulfate can be remarkably increased over the conventional processes. For instance, in FIG. 1, line AB represents the solubility (i.e. the saturated molar concentration) of cerous sulfate corresponding to the molar concentration of ceric sulfate in the aqueous sulfuric acid solution, where A represents the saturated molar concentration of cerous sulfate in the aqueous sulfuric acid solution, and B represents the saturated molar concentration of ceric sulfate. Further, $l_1$, $l_2$ and $l_3$ in FIG. 1 represent the compositions (molar concentrations of ceric sulfate and cerous sulfate) in the 6% sulfuric acid aqueous solution in Table 1, prior to the oxidation reaction. Namely, the composition of $[Ce(SO_4)_2$ and $Ce_2(SO_4)_3]$ (molar concentrations) in the 6% sulfuric acid aqueous solution prior to the oxidation reaction is [0.67 mol/liter (saturation) and 0 mol/liter] at $l_1$, [0.67 mol/liter and 0.1 mol/liter] at $l_2$ and [0.67 mol/liter and 0.15 mol/liter] at $l_3$. When the oxidation reaction is conducted with use of a ceric sulfate-aqueous sulfuric acid solution having a composition of $l_1$, $l_2$ or $l_3$, the composition in the aqueous sulfuric acid solution will change towards the composition of $m_1$, $m_2$ or $m_3$, respectively, in FIG. 1. If the change exceeds $m_1$, $m_2$ or $m_3$, cerous sulfate will precipitate. Accordingly, in the case of the 6% sulfuric acid aqueous solution as shown in FIG. 1, ceric sulfate capable of changing from $l_1$, $l_2$ and $l_3$ to $m_1$, $m_2$ and $m_3$, respectively, represents the maximum effective amount of ceric sulfate suitable for the reaction of the present invention. Likewise, in the case of the 10% sulfuric acid aqueous solution as shown in FIG. 2, ceric sulfate capable of changing from $l'_1$, $l'_2$ and $l'_3$ to $m'_1$, $m'_2$ and $m'_3$, respectively, in FIG. 2 represents the maximum effective amount of ceric sulfate suitable for the purpose of the present invention, and in the case of the 14% sulfuric acid aqueous solution as shown in FIG. 3, ceric sulfate capable of changing from $l''_1$, $l''_2$ and $l''_3$ to $m'_1$, $m'_2$ and $m'_3$, respectively, in FIG. 3 likewise represent the maximum effective amount of ceric sulfate suitable for the purpose of the present invention.

Whereas, in the conventional processes, the molar concentration of cerium (ions) of cerous sulfate corresponding to the saturated molar concentration (shown at point A in each of FIGS. 1 to 3) of cerous sulfate in the aqueous sulfuric acid solution having a concentration of e.g. 6%, 10% or 14%, is considered to correspond practically to the limit of the molar concentration of ceric sulfate in the aqueous sulfuric acid solution, since it is desired that cerous sulfate formed by the oxidation reaction is dissolved in the aqueous sulfuric acid solution. For instance, in each of FIGS. 1 to 3, the saturated molar concentration of cerous sulfate in the aqueous sulfuric acid solution, as shown at point A, is calculated on the basis that one mol contains two cerium atoms. Accordingly, the maximum effective amount of ceric sulfate in the conventional processes, corresponds to twice the value obtained by subtracting the molar concentration of cerous sulfate in each aqueous sulfuric acid solution prior to the oxidation reaction (i.e. in FIG. 1: $l_1=0$ mol/liter, $l_2=0.1$ mol per liter; in FIG. 2: $l'_1=0$ mol/liter, $l'_2=0.1$ mol per liter; in FIG. 3: $l''_1=0$ mol/liter, $l''_2=0.1$ mol/liter) from the corresponding saturated concentration of cerous sulfate shown at point A (i.e. in FIG. 1: 0.125 mol/liter; in FIG. 2: 0.115 mol/liter; in FIG. 3: 0.110 mol per liter). Accordingly, in the conventional processes, a concentration higher than the saturated molar concentration of cerous sulfate shown at point A in each of FIGS. 1 to 3, e.g. in the case of $l_3$, $l'_3$ or $l''_3$ in FIGS. 1, 2 or 3, has not practically been employed.

The maximum effective amounts of ceric sulfate in the process of the present invention and in the conventional processes, as obtained in the same manner as described above, are shown in Table 1 for the purpose of comparison.

Reaction condition:
Temperature: 50° C., sulfuric acid concentration after the reaction: 6%, 10% or 14%.
Before the reaction:
$Ce(SO_4)_2$ concentration: saturated molar concentration
$Ce_2(SO_4)_3$ concentration: 0 mol/liter, 0.1 mol/liter or 0.15 mol/liter.
After the reaction:
$Ce(SO_4)_2$ concentration: maximum molar concentration capable of dissolving cerous sulfate present.
$Ce_2(SO_4)_3$ concentration: maximum molar concentration without precipitation.

TABLE 1

| Sulfuric acid concentration (after the reaction) | Process of the present invention | | | | Conventional processes Maximum effective amount of $Ce(SO_4)_2$ |
|---|---|---|---|---|---|
| | Before and after the reaction | Changes of the compositions of the cerium sulfate solutions | | Maximum effective amount of $Ce(SO_4)_2$ | |
| | | $Ce(SO_4)_2$ (mol/liter) | $Ce_2(SO_4)_3$ (mol/liter) | | |
| 6% | Before $l_1$ | 0.67 | 0.0 | 0.40 | 0.25 |
| | After $m_1$ | 0.27 | 0.20 | | |
| | Before $l_2$ | 0.67 | 0.1 | 0.28 | 0.05 |
| | After $m_2$ | 0.39 | 0.24 | | |
| | Before $l_3$ | 0.67 | 0.15 | 0.21 | — |
| | After $m_3$ | 0.46 | 0.255 | | |
| 10% | Before $l'_1$ | 0.50 | 0.0 | 0.33 | 0.23 |
| | After $m'_1$ | 0.17 | 0.165 | | |
| | Before $l'_2$ | 0.50 | 0.1 | 0.19 | 0.03 |
| | After $m'_2$ | 0.31 | 0.19 | | |
| | Before $l'_3$ | 0.50 | 0.15 | 0.12 | — |
| | After $m'_3$ | 0.38 | 0.21 | | |
| 14% | Before $l''_1$ | 0.40 | 0.0 | 0.28 | 0.22 |
| | After $m''_1$ | 0.12 | 0.14 | | |
| | Before $l''_2$ | 0.40 | 0.1 | 0.14 | 0.02 |
| | After $m''_2$ | 0.26 | 0.17 | | |
| | Before $l''_3$ | 0.40 | 0.15 | 0.07 | — |
| | After $m''_3$ | 0.33 | 0.185 | | |

As is evident from the results of Table 1, the process of the present invention is industrially superior to the conventional processes particularly in that the maximum effective amount of ceric sulfate is remarkably high as compared with the conventional processes. Further, it is thereby possible to increase the current efficiency in the electrolytic oxidation of cerous sulfate for regeneration by maintaining the concentration of cerous sulfate at a level of at least 0.1 mol/liter. This is another remarkable effect of the present invention which has a substantial merit from the industrial point of view.

The process of the present invention is usually conducted in the following manner.

Namely, to a ceric sulfate-aqueous sulfuric acid solution having a predetermined composition, an organic compound i.e. the starting material is added as dissolved or not dissolved in a water-immiscible organic solvent in the presence or absence of cerous sulfate and optionally in the presence of a dispersing agent, and then the mixture is stirred at a predetermined temperature to conduct the oxidation reaction. The amount or reaction rate of ceric sulfate relative to the starting material organic compound is adjusted so that it is capable of dissolving cerous sulfate at the end of the reaction. After the reaction, the oxidation reaction product of the organic compound is separated by e.g. a liquid-liquid separation of the organic solvent solution or filtration, and if necessary, the oxidation reaction product dissolved in the aqueous layer is extracted with a solvent and the oxidation reaction product in the solvent thus obtained may be collected by removing the solvent or may be used as it is as a starting material for a subsequent reaction. The separated aqueous layer is usually subjected to electrolytic oxidation, whereby cerous sulfate formed by the oxidation reaction with ceric sulfate, is regenerated as ceric sulfate, which will be recycled for reuse.

As the organic solvent, there may be mentioned an aromatic hydrocarbon or its substituted derivative such as benzene, ethylbenzene, a tert-alkylbenzene such as tert-butylbenzene or chlorobenzene; an aliphatic hydrocarbon such as n-hexane, n-pentane or n-octane; or a chlorinated aliphatic hydrocarbon such as carbon tetrachloride, chloromethylene, dichloroethane, trichloroethane or tetrachloroethane.

The electrolytic oxidation of cerous sulfate to ceric sulfate is usually conducted in a forced circulation diaphragm-type electrolytic cell. As the anode, there may be used an electrode made of lead dioxide-coated titanium, platinum-plated titanium, iridium-titanium or platinum-iridium-titanium. As the cathode, there may be employed, in addition to the above electrodes, an electrode made of stainless steel (SUS 316 or SUS 316L). As the diaphragm, there may be employed a cation exchange membrane, an anion exchange membrane or a non-polar diaphragm. However, it is usually preferred to employ a fluorinated ion exchange membrane. The temperature for the electrolysis is usually from 30° to 80° C.

The oxidation reaction with ceric sulfate is usually conducted under atmospheric pressure. However, the oxidation reaction may be conducted under an elevated pressure. The oxidation reaction may be conducted in a batch system or in a continuous system. For instance, it may be conducted in a counter current system wherein the above oxidation reaction is combined with a liquid-liquid separation of the oxidation reaction product with an organic solvent.

Now, the present invention will be described in further detail with reference to Examples. However, it should be understood that the present invention is by no means restricted by these specific Examples. In this specification, "%" means "% by weight" unless otherwise specified.

EXAMPLE 1

Into a bottom-discharge type glass-lined reactor equipped with a stirrer with flat turbine vanes and a temperature controlling means, 41.5 g (0.125 mol) of ceric sulfate was introduced, and 10% sulfuric acid was added under stirring to bring the total amount to about 250 ml at about 50° C. The concentration of ceric sulfate was about 0.5 mol/liter. This aqueous sulfuric acid solution was heated to 55° C., and 2.56 g (0.02 mol) of naphthalene and 6.8 g of tert-butylbenzene were added. The mixture was forcibly stirred at 60° C. for about 30 minutes. After the completion of the reaction, the stirrer was stopped, and the aqueous layer was withdrawn from the bottom of the reactor.

The aqueous layer thus withdrawn, was extracted twice with 10 g of tert-butylbenzene, and the extraction oil layer thereby obtained was combined with the solvent layer previously separated from the aqueous layer. The formed 1,4-naphthoquinone and unreacted naphthalene in the total organic solvent were quantitatively analyzed by a high speed liquid chromatography.

On the other hand, in the above-mentioned aqueous layer, no precipitation of crystals of cerous sulfate was observed. The by-product phthalic acid contained in this aqueous layer was analyzed in the following manner and the amount of the product was measured. Namely, 2.00 g of a sample of the above aqueous layer was taken, and after an addition of an internal standard solution, a solvent mixture of methanol-water corresponding to the composition of the developer used in the high speed liquid chromatography, was added thereto, whereby cerous sulfate and ceric sulfate were precipitated, then the crystals were separated by filtration and the filtrate was subjected to a quantitative analysis by a high speed liquid chromatography.

As the results, it was found that the amount of formed 1,4-naphthoquinone was 1.66 g (0.0105 mol) (52.5 molar % relative to the starting material naphthalene), the amount of formed phthalic acid was 0.061 g (0.00037 mol) (1.9 molar % relative to the starting material naphthalene), and the amount of unreacted naphthalene was 1.15 g (0.0090 mol) (45.0 molar % relative to the starting material naphthalene). Namely, the yield of 1,4-naphthoquinone relative to reacted naphthalene was 95 molar %, and the yield of the by-product phthalic acid was 3 molar % relative to reacted naphthalene. Further, the concentration of ceric sulfate in the aqueous layer was 0.21 mol/liter and the concentration of cerous sulfate therein was 0.15 mol/liter.

EXAMPLE 2

Into the same reactor as in Example 1, 41.5 g (0.125 mol) of ceric sulfate and 17.1 g (0.03 mol) of cerous sulfate were introduced, and 10% sulfuric acid was added to bring the total volume to about 250 ml at about 50° C. The concentration of ceric sulfate was about 0.5 mol/liter, and the concentration of cerous sulfate was about 0.12 mol/liter. Then, the aqueous sulfuric acid solution was heated to 55° C., and 2.56 g (0.02 mol) of naphthalene and 6.8 g of tert-butylbenzene were added. The mixture was forcibly stirred at 60° C. for about 10 minutes. After the completion of the reaction, the stirrer was stopped, and the aqueous layer was withdrawn from the bottom of the reactor.

Thereafter, the withdrawn aqueous layer and the tert-butylbenzene layer were analyzed, respectively, in the same manners as in Example 1.

As the results, the amount of formed 1,4-naphthoquinone was 0.702 g (0.00444 mol) (22.2 molar % relative to the starting material naphthalene), the amount of formed phthalic acid was 0.026 g (0.0154 mol) (0.8 molar % relative to the starting material naphthalene), and the amount of unreacted naphthalene was 1.97 g (76.9 molar % relative to the starting material naphthalene). Thus, yield of 1,4-naphthoquinone relative to reacted naphthalene was 96 molar %, and the yield of the by-product phthalic acid was 3 molar %.

On the other hand, the concentration of ceric sulfate in the withdrawn aqueous layer was 0.38 mol per liter, and the concentration of cerous sulfate therein was 0.18 mol/liter. The aqueous layer was a uniform solution, wherein no precipitation of crystals of cerous sulfate was observed.

Then, the above aqueous layer was continuously supplied to an anolyte circulating line partitioned by a cation exchange membrane, while an aqueous sulfuric acid solution was supplied as a catholyte, whereby electrolytic oxidation was conducted for regeneration at about 55° C. by using platinum electrodes until the concentration of ceric sulfate reached to a level of 0.5 mol/liter. The current efficiency was at least 95%.

The regenerated ceric sulfate-aqueous sulfuric acid solution thus obtained was added to the same tert-butylbenzene solution of naphthalene as mentioned above. The mixture was reacted in the same manner as above and then treated in the same manner as above, followed by similar analyses, whereby substantially the same results as above were obtained.

EXAMPLE 3

Into the same reactor as in Example 1, 52.7 g of ceric sulfate hydrate [78.5% as Ce(SO$_4$)$_2$, the rest being water of crystallization], 21.4 g of cerous sulfate hydrate [79.8% as Ce$_2$(SO$_4$)$_3$, the rest being water of crystallization] and 241 g of a 8% sulfuric acid aqueous solution, were introduced, and the mixture was heated to 45° C. and dissolved. The total volume was 250 ml, the concentration of ceric sulfate was 0.50 mol/liter and the concentration of cerous sulfate was 0.12 mol/liter. Then, to the reactor, a solution of 2.67 g of crude naphthalene (purity 95.5%) in 14.0 g of ethylenedichloride was added, and the reaction was conducted at 50° C. for 30 minutes under forcible stirring. After the completion of the reaction, the reaction mixture was left to stand still, and the oil layer was withdrawn from the bottom of the reactor.

The aqueous layer separated from the oil layer was subjected to an extraction operation whereby 1,4-naphthoquinone was extracted twice with use of 10 g of ethylenedichloride. The extraction oil layer thus obtained, was combined with the ethylenedichloride solution of the oil layer withdrawn as mentioned above. Then, 1,4-naphthoquinone and unreacted naphthalene in the total ethylenechloride solution, and the by-product phthalic acid in the aqueous layer, were quantitatively analyzed in the same manner as in Example 1.

As the results, the amount of formed 1,4-naphthoquinone was 0.707 g (22.5 molar % relative to the starting material naphthalene), the amount of formed phthalic acid was 0.023 g (0.70 molar % relative to the starting material naphthalene) and the amount of unreacted naphthalene was 1.95 g (76.5 molar % relative to the starting material naphthalene). Thus, the yield of 1,4-naphthoquinone relative to reacted naphthalene was 95.1 molar %, and the yield of the by-product phthalic acid was 3.0 molar %.

On the other hand, the concentration of ceric sulfate in the aqueous layer separated from the oil layer was 0.37 mol/liter, and the concentration of cerous sulfate was 0.18 mol/liter. The aqueous layer was a uniform solution, wherein no precipitation of cerous sulfate was observed.

Figure 4:
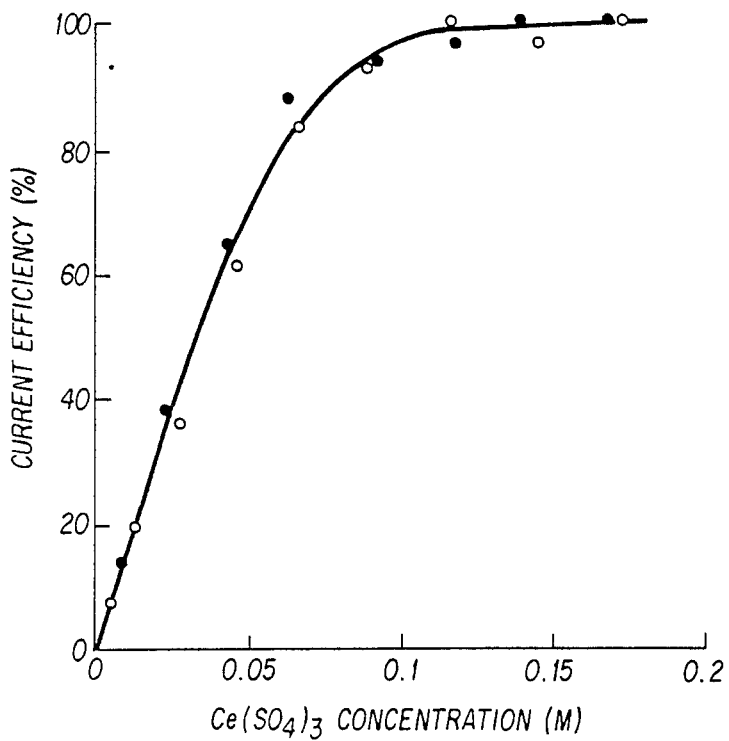
FIG. 4 is a graph showing the relation of the current efficiency to the cerous sulfate concentration in an aqueous solution of a cerous sulfate-ceric sulfate-sulfuric acid system.

FIG. 4 illustrates the relation between the current efficiency relative to the cerous sulfate concentration in the electrolytic oxidation of an aqueous solution of cerous sulfate-ceric sulfate-sulfuric acid system. The working condition of the electrolysis was as follows:

Anode:
  Pt/Ti ... Symbol ◯ in FIG. 4
  Pt.Ir/Ti ... Symbol ● in FIG. 4
Cathode: SUS 316L
Membrane: Selemion CMF
Temperature for electrolysis: 50° C.
Linear velocity of electrolyte: 0.4 m/S
Current density: 16.3 A/dm$^2$
Concentration of the aqueous sulfuric acid solution: 10% by weight.

We claim:

1. A process for oxidizing an oxidizable organic compound by ceric sulfate dissolved in an aqueous sulfuric acid solution, wherein the organic compound is oxidized (1) by means of a ceric sulfate-aqueous sulfuric acid solution or a cerous sulfate-containing ceric sulfate-aqueous sulfuric acid solution in which the molar concentration (mol/liter) of ceric sulfate is (i) at least the molar concentration of cerium (ions) contained in the molecules of cerous sulfate at the maximum solubility of cerous sulfate in an aqueous sulfuric acid solution at the final sulfuric acid concentration (exclusive of ceric sulfate and cerous sulfate) and at the temperature under the oxidation reaction conditions and (ii), at most the saturated molar concentration of ceric sulfate in said aqueous sulfuric acid solution, (2) under a condition such that at the end of the oxidation reaction, the concentration of ceric sulfate is maintained at a level capable of dissolving cerous sulfate which is present at a concentration of at least the maximum solubility of cerous sulfate in said aqueous sulfuric acid solution.

2. The process according to claim 1, wherein the final sulfuric acid concentration of the aqueous sulfuric acid solution is from about 5 to about 15% by weight.

3. The process according to claim 1, wherein the final sulfuric acid concentration of the aqueous sulfuric acid solution is from about 6 to about 12% by weight.

4. The process according to claim 1, wherein the oxidation reaction is conducted at a temperature of from 40° to 80° C.

5. The process according to claim 1, wherein the final sulfuric acid concentration in the aqueous sulfuric acid solution is from about 6 to about 10% by weight, the reaction temperature is from 40° to 60° C., and the concentration of ceric sulfate prior to the reaction is at least 0.28 mol/liter and at most the saturated molar concentration.

6. The process according to claim 1, wherein the concentration of ceric sulfate is at least 0.3 mol/liter and at most the saturated molar concentration.

7. The process according to claim 1, wherein the aqueous sulfuric acid solution prior to the oxidation reaction contains, in addition to ceric sulfate, from 0.1 to 0.18 mol/liter of cerous sulfate.

* * * * *